United States Patent [19]

Degen et al.

[11] Patent Number: 5,567,615
[45] Date of Patent: Oct. 22, 1996

[54] AFFINITY SEPARATION METHOD

[75] Inventors: Peter J. Degen, Huntington, N.Y.; Tony Alex, Kendall Park, N.J.; Richard F. Salinaro, Hastings on Hudson, N.Y.

[73] Assignee: Pall Corporation, East Hills, N.Y.

[21] Appl. No.: 396,343

[22] Filed: Feb. 28, 1995

Related U.S. Application Data

[63] Continuation of Ser. No. 172,475, Dec. 23, 1993, abandoned.

[51] Int. Cl.$^6$ ............................ C12P 1/00; C07K 1/22; A61K 39/395; C02F 1/28
[52] U.S. Cl. ............................ 435/280; 435/803; 435/41; 530/413; 530/344; 530/417; 424/124; 424/157.1; 210/691; 210/767
[58] Field of Search ............................ 435/177, 2, 41, 435/178, 803, 180, 280, 261; 210/502, 660, 691, 767; 530/413, 344, 417; 622/70; 424/124, 157.1; 935/108

[56] References Cited

U.S. PATENT DOCUMENTS

| | | |
|---|---|---|
| 3,088,875 | 5/1963 | Fisk . |
| 3,796,634 | 3/1974 | Haynes et al. . |
| 3,797,662 | 3/1974 | Titus . |
| 3,956,065 | 5/1976 | Idaszak et al. . |
| 3,997,447 | 12/1976 | Breton et al. . |
| 4,045,353 | 8/1977 | Kosaka ............................ 210/502 |
| 4,059,685 | 11/1977 | Johnson . |
| 4,066,554 | 1/1978 | Guyer . |
| 4,092,114 | 5/1978 | Buck . |
| 4,093,552 | 6/1978 | Guyer . |
| 4,105,426 | 8/1978 | Iler et al. . |
| 4,143,203 | 3/1979 | Rigopulos et al. . |
| 4,210,722 | 7/1980 | Silver . |
| 4,278,651 | 7/1981 | Takaya . |
| 4,335,017 | 7/1982 | Miles et al. . |
| 4,352,884 | 10/1982 | Nakashima et al. . |
| 4,357,142 | 11/1982 | Schall, Jr., et al. . |
| 4,357,311 | 11/1982 | Schutt . |
| 4,416,813 | 11/1983 | Ikeda et al. . |
| 4,418,152 | 11/1983 | Hosaka et al. . |
| 4,421,850 | 12/1983 | Daniels et al. . |
| 4,427,552 | 1/1984 | Lieberherr et al. . |
| 4,536,478 | 8/1985 | Sokoloff et al. . |
| 4,547,466 | 10/1985 | Turanchik et al. . |
| 4,563,431 | 1/1986 | Pauly et al. . |
| 4,590,169 | 5/1986 | Cragle et al. . |
| 4,591,571 | 5/1986 | Kuboyama et al. . |
| 4,629,690 | 12/1986 | Weng et al. . |
| 4,663,278 | 5/1987 | DiNello . |
| 4,680,274 | 7/1987 | Sakai et al. . |
| 4,720,465 | 1/1988 | Jensen et al. . |
| 4,732,851 | 3/1988 | Wood et al. . |
| 4,806,488 | 2/1989 | Berger, Jr. et al. . |
| 4,900,440 | 2/1990 | Ziegler et al. . |
| 4,952,317 | 8/1990 | Culkin . |
| 4,956,102 | 9/1990 | Allsing . |
| 5,037,562 | 8/1991 | Tarves, Jr. . |
| 5,077,210 | 12/1991 | Eigler et al. . |
| 5,135,653 | 8/1992 | Okamoto et al. ............................ 210/635 |
| 5,143,630 | 9/1992 | Rolchigo ............................ 210/780 |
| 5,167,824 | 12/1992 | Cohen et al. ............................ 210/638 |
| 5,248,611 | 9/1993 | Benkovic et al. ............................ 435/280 |

FOREIGN PATENT DOCUMENTS

| | | |
|---|---|---|
| 1223859 | 7/1987 | Canada . |
| 0084666 | 8/1983 | European Pat. Off. . |
| 1198835 | 7/1970 | United Kingdom . |
| 2113226 | 8/1983 | United Kingdom . |
| 2275626 | 9/1994 | United Kingdom . |
| WO87/04169 | 7/1987 | WIPO . |
| WO94/11103 | 5/1994 | WIPO . |

OTHER PUBLICATIONS

Scharschmidt et al, *J. Lab. Clin. Med.*, vol. 89, pp. 101–108, 1977.

"Chromatography, Affinity," *Kirk–Othmer Encyclopedia of Chemical Technology*, 6, 35–54 (John Wiley & Sons: New York, 1979).

*Chem. Eng. Prog.*, "Fluid Flow Through Packed Columns", 48, 89–94 (1952).

Chen et al., "Chemical Procedures For Enzyme Immobilization of Porous Cellulose Beads," *Biotechnology and Bioengineering*, XIX, 1463–1473 (1977).

"Epoxy Activated Sepharose", *Pharmacia Fine Chemicals* (Affinity Chromatography), 6B, 27–32 (1979).

Svec et al., "Immobilization of Amyloglucosidose on Poly [(Glycidyl Methacrylate) Co (Ethylene Dimethacrylate)] Carrier and Its Derivatives", *Biotechnology and Bioengineering*, XX, 1319–1328 (1978).

Hoffman et al., "New Approaches to Non–Thrombogenic Materials", *Coagulation–Current Research and Clinical Applications*, (Academic Press, New York 1973).

Murkes, "Fundamentals of Crossflow Filtration", *Separation and Purification Methods*, 19 (1), 1–29 (1990).

"Enzyme Technology" (Noyes Data Corporation 1983), 38–107.

Pungor, Jr. et al., "Continuous Affinity–Recycel Extraction: A Novel Protein Separation Technique", *Bio/Technology*, 5, 604–608 (1987).

Nguyen et al., "Syntheses and Applications of Water–Soluble Reactive Polymers for Purification and Immobilization of Biomolecules", *Biotechnology and Bioengineering*, 34, 1186–90 (1989).

Eveleigh et al., "Immunochemical Characteristics and Preparative Application of Agarose–Based Immunosorbents[1, 2]", *Journal of Solid–Phase Biochemistry*, 2 (1), 45–78 (1977).

Chase, "Scale–up of Immunoaffinity Separation Processes", *Journal of Biotechnology*, 1, 67–80 (1984).

Belter et al., "An Overview of Bioseparations", *Bioseparations Downstream Processing for Biotechnology*, Chapter 1, 1–9.

*Primary Examiner*—Irene Marx
*Attorney, Agent, or Firm*—Leydig, Voit & Mayer, Ltd.

[57] ABSTRACT

The present invention provides an affinity separation method involving dynamic filtration.

34 Claims, 2 Drawing Sheets

AFFINITY SEPARATION METHOD

This is a continuation of application Ser. No. 08/172,475 filed Dec. 23, 1993, now abandoned.

TECHNICAL FIELD OF THE INVENTION

The present invention relates to the isolation and separation of compounds from fluids. The present invention is an improved affinity separation method, which is particularly useful in the isolation of biologically active compounds.

BACKGROUND OF THE INVENTION

Advances in engineering have made possible the production of commercial quantities of therapeutically useful proteins which heretofore have been too complex or expensive to manufacture through traditional biochemical processes. Manufacturing is accomplished by cells that are engineered to produce a desired protein and can be grown in bioreactors under controlled conditions. The technology used involves either the fermentation of microorganisms which have been altered through recombinant DNA techniques or the culturing of mammalian cells which have been altered through hybridoma techniques. The cells are suspended in a broth which contains the salts, sugars, proteins, and various factors necessary to support the growth of particular cells. The desired protein may be either secreted by the cells into the broth or retained within the cell body.

Other proteins of interest can be prepared using alternative means, such as by genetically altering an animal species in order to provide the animal with the capability of producing the desired protein. For example, certain proteins can be produced by transgenic cows and harvested from their milk.

The separation, or purification, of these proteins from a heterogenous mixture has proven to be a formidable task for at least the following reasons: the desired protein often represents a small percentage of total protein; the broth or other liquid to be processed may contain significant quantities of cell debris and other particulate contaminants; pyrogens, pathogens, toxins, and other contaminants may be present in high concentration and must be removed; and the desired protein must be separated from the heterogenous protein solution without denaturing it.

As a result of these factors, extensive downstream processing has been necessarily used to yield high quantities of purified protein. Such downstream processing includes the many stages of processing that take place subsequent to the production of the protein of interest including, for example, centrifugation, cell disruption, mechanical sieving, microfiltration, ion-exchange, cross-flow filtration, affinity separation, sterilization, purification, and packaging. The downstream processing represents a major cost in the production of bioprocessed proteins. Thus, a method which efficiently provides high yielding protein separation by reducing the number of processing steps, and which can be used on an industrial scale, would further the successful commercialization of biotechnology.

It is known that many compounds complex with ligands such that those compounds may be isolated by a technique known as affinity separation. See generally "Chromatography, Affinity," *Kirk-Othmer Encyclopedia of Chemical Technology*, 6, 35–54 (John Wiley & Sons: New York, 1979). This method of separation involves three phases: (i) an adsorption phase, wherein the desired compound, such as a protein, from a heterogenous mixture forms a complex with a chemical functionality, such as a ligand, bound to an insoluble substrate, such as a polymeric or glass bead, (ii) a washing phase wherein the bulk of the solution is washed away along with contaminants loosely bound to the insoluble substrate, and (iii) an elution stage wherein an eluant breaks the complex between the desired compound and the ligand bound to the insoluble substrate so as to release the desired compound. The insoluble substrate with the bound ligand, which is referred to as the affinity particles, may be washed and reused, and the method may be repeated numerous times.

The affinity particles are typically selected based upon surface area per unit mass. For example, while nonporous spherical beads of 100 microns diameter may provide a surface area of 0.06 $m^2/g$ of beads, similar beads of 1 micron diameter would provide a surface area of 6.0 $m^2/g$ of beads, and beads of 0.1 micron diameter would provide a surface area of 60 $m^2/g$ of beads. Clearly, smaller affinity particles provide a larger surface area per unit weight and are more desirable. In affinity separation, it is generally desirable to utilize affinity particles which have a surface area of greater than about 20 $m^2/g$. Thus, if one desires to use nonporous affinity particles in an affinity separation process, such affinity particles must have a diameter in the submicron range.

The most widely practiced form of affinity separation is affinity chromatography. Affinity chromatography utilizes a column of tightly packed affinity particles through which the fluid (e.g., liquid feed stream) containing the target compound, such as a protein, is forced under pressure. The hydrodynamics of a packed or fixed bed system such as this is governed by the Ergun equation. *Chem. Eng. Prog.*, 48 (1952). The Ergun equation, which is used when the bed experiences laminar flow of fluid, demonstrates that the pressure drop across the bed is inversely proportional to the square of the particle diameter. When calculated, the pressure drops of systems which use submicron affinity particles are in the order of one million times greater than those packed with 100 micron particles. This effect has heretofore prevented the use of such small affinity particles in affinity separations. Consequently, the typical bed utilizes affinity particles of about 100 microns in size to maintain an acceptable pressure drop.

Attempts have been made to overcome the problems associated with nonporous affinity particles with respect to providing a high surface area per unit weight. In particular, the nonporous affinity particles have been substituted with porous affinity particles. In typical applications, porous beads of about 100 microns in diameter provide a surface area in the range of about 40 $m^2/g$ per bead under moderate pressure drop conditions.

The use of porous affinity particles, however, creates additional problems which are not experienced by nonporous affinity particles. For reasons not entirely understood, but perhaps relating to plugging and diffusional resistance, only the outer about 5 percent of the porous region of the affinity particle is generally accessible to the substance sought to be separated. This results in the effective surface area of the porous affinity particle being much less than the total theoretically available surface area. While the pretreatment of the feed stream could prevent at least a portion of the plugging and diffusional resistance of the porous affinity particles, such pretreatment of the feed stream involves a costly and time consuming series of steps. Further, each additional processing step serves to increase the loss of the target compound and thereby reduce productivity.

Moreover, because the majority of the total surface area in the porous affinity particles is interior of the surface of the affinity particles, mass transfer effectively controls the separation process, thereby resulting in time consuming and laborious separations. Further, the pores of the affinity particles can act as traps for unwanted compounds and debris and can eventually cause contamination of the desired compound. Also, as the pores in the affinity particles gradually plug, the effectiveness of the affinity particles is decreased with each succeeding cycle. In addition, the mechanical strength of the affinity particles is reduced due to the presence of the pores, which results in poor abrasion resistance and mechanical stability and may result in affinity particle collapse at high pressures. The porous affinity particles also swell as they are packed in a bed, which requires the adjustments to be made for this phenomenon.

Another consideration of column techniques which is affinity particle-independent is that, in order to achieve high flow rates, the column must have a large capacity. Tall columns, however, result in such high pressures at the lower zone of the columns that they deform the affinity particles and reduce throughput. The industry has attempted to overcome this problem by designing columns which are short and rather wide. This compromise, however, is not entirely satisfactory, since efficiency is greatly reduced due to flow problems like channeling and departure from plug flow.

Columns also exhibit a concentration wave phenomenon that results in a low effective utilization of adsorbent. Specifically, as feed passes through the column, only a small zone of affinity particles is utilized in a particular time frame since the entrance zone is already saturated with the target compound. This results in a concentration wave phenomenon where only the wave front interacts with the adsorbent at a given moment.

In order to overcome the disadvantages inherent in fixed beds and the problems which arise when porous affinity particles are used therein, researchers have turned their attention toward moving bed affinity separation systems.

A fluidized bed is one type of moving bed affinity system. In such a bed, the feed stream is pumped up from the bottom of a column, causing the affinity particles to act like a fluid. As a result, fluidized beds do not exhibit concentration wave characteristics. Moreover, all the affinity particles are exposed to the feed stream simultaneously. Fluidized beds offer higher productivity than columns as a result of the efficient utilization of the affinity particles and increased throughput. Further, these beds can accept a higher level of particulate debris and still function relatively efficiently as compared to fixed bed systems.

A drawback with fluidized beds, however, is that efficiencies limit both the size and density of the affinity particles that can be used in such systems, i.e., it is necessary to maximize density and optimize size. This is because, generally, a major part of the separation process is controlled by the settling velocity of the affinity particles. Thus, the higher the density of the affinity particles used, the faster the affinity particles will settle, thereby enabling the use of higher fluidization velocities. An increase in the fluidization velocity will result in a higher throughput and, therefore, higher efficiency, until the upper limit of the rate of kinetics is reached. While the rate of kinetics can be increased by reducing the size of the affinity particles (thereby increasing the total available surface area), the increase of the rate of kinetics also has the negative effect of limiting the fluidization velocity that can be achieved, thereby lowering efficiency. These competing considerations require that compromises be made with regard to the size and density of the affinity particles, and these compromises prevent this type of system from reaching higher efficiencies.

Another type of moving bed system, referred to as a stirred tank system, also offers significant benefits over fixed bed columns. In a stirred tank system, affinity particles are kept suspended in a tank by mechanical means. This mixing action allows the suspension to behave like a homogeneous fluid, thereby exposing all the particles to the target compound simultaneously. This process can therefore be designed as a loop, with a significant increase in productivity. The affinity particles in such a system are preferably sufficiently buoyant to allow for a stable suspension in the process fluid. Since there is less packing in this system, the preferred diameter of the affinity particles is typically smaller than in a column or fluidized bed, which allows for an increase in surface area. A major limitation of stirred tanks is that the filters used for the wash and elution stages foul as a result of the crude nature of the feed stock. Thus, the feed stream must typically be pretreated, thereby adding an additional processing step and reducing the overall system efficiency.

In each of these various conventional affinity separation processes, there are multiple processing steps. While each step may have an efficiency or product yield of 80–90%, the existence of only a few processing steps can easily reduce the overall system efficiency and product yield to 50% or less. With each additional processing step, the overall system efficiency is even further lowered.

Thus, there exists a need for a method which avoids these many problems inherent in the existing affinity separation processes and provides a more efficient means for isolating and separating compounds, such as proteins and the like, from a fluid, e.g, a dilute liquid feed stream. The present invention provides such a method. The present inventive method involves an affinity separation process with fewer processing steps which can be carried out in a relatively short period of time and with an increased overall efficiency to remove a desired compound from a fluid. Moreover, the present inventive method overcomes the problems of fouling as regarding both the affinity particles and filtration medium which hamper the kinetics and flow-through of the system, without the need to pretreat the fluid containing the desired compound. Further, a wide variety of affinity particles varying in both density and size, including small affinity particles with a high surface area per unit of weight can be used successfully in the affinity separation method of the present invention, thereby enabling the system to be customized to achieve greater efficiencies for particular end uses. These and other objects and advantages of the present invention, as well as additional inventive features, will be apparent from the description of the invention provided herein.

BRIEF SUMMARY OF THE INVENTION

The present invention provides an improved affinity separation method comprising (a) introducing affinity particles and a fluid containing a target compound to be isolated which is capable of adsorbing onto the affinity particles into a dynamic filtration apparatus comprising motive means, a filtration medium having upstream and downstream sides, an inlet in fluid communication with the upstream side of the filtration medium, and a filtrate outlet in fluid communication with the downstream side of the filtration medium, wherein the fluid is capable of passing through the filtration medium and the affinity particles are substantially incapable of passing through the filtration medium, (b) operating the motive means of the dynamic filtration apparatus with the filtrate outlet being in a closed position such that the fluid cannot pass through the filtration medium under conditions sufficient to allow for the target compound to adsorb onto the affinity particles, and (c) separating the affinity particles from the fluid by opening the filtrate outlet so as to allow the fluid to pass through the filtration medium of the dynamic filtration apparatus. The filtrate can be thereby rendered substantially free of the target compound. If the recovery of the target compound is desired and/or if the affinity particles are to be reused, the affinity particles are then washed, and the target compound is eluted from the affinity particles.

DESCRIPTION OF THE PREFERRED EMBODIMENTS

Figure 1:
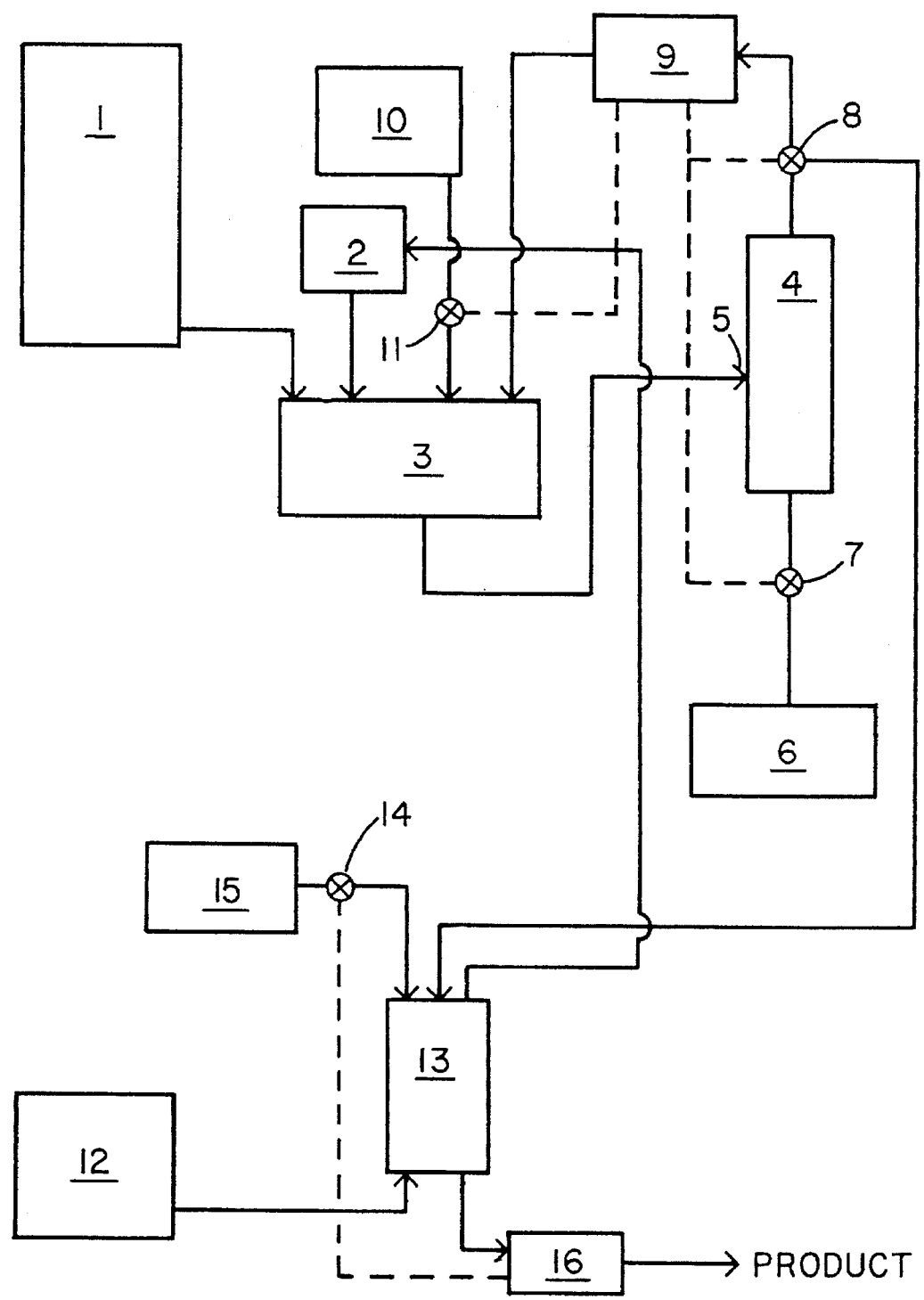
FIG. 1 is a schematic depiction of the significant elements used in a preferred embodiment of the present invention.

The present invention provides an improved affinity separation method. In particular, it has been surprisingly found that the use of a dynamic filtration apparatus can be used to efficiently effect contact between a fluid containing a desired (or target) compound and affinity particles and that the dynamic filtration apparatus can thereafter be used to separate the fluid from the affinity particles having the adsorbed or complexed compound thereon. Such a process enables the use of affinity particles having small diameters and relatively large surface areas per weight of the affinity particles.

The present inventive method is an improved affinity separation method comprising:

(a) introducing affinity particles and a fluid containing a target compound to be isolated which is capable of adsorbing onto the affinity particles into a dynamic filtration apparatus comprising motive means, a filtration medium having upstream and downstream sides, an inlet in fluid communication with the upstream side of the filtration medium, and a filtrate outlet in fluid communication with the downstream side of the filtration medium, wherein the fluid is capable of passing through the filtration medium and the affinity particles are substantially incapable of passing through the filtration medium, (b) operating the motive means of the dynamic filtration apparatus with the filtrate outlet being in a closed position such that the fluid cannot pass through the filtration medium under conditions sufficient to allow for the target compound to adsorb onto the affinity particles, and (c) separating the affinity particles from the fluid by opening the filtrate outlet so as to allow the fluid to pass through the filtration medium of the dynamic filtration apparatus.

The fluid can be thereby rendered substantially free of the target compound. If the recovery of the target compound is desired and/or if the affinity particles are to be reused, then the affinity particles are washed, and the target compound is eluted from the affinity particles.

The present inventive method provides for the exceptionally efficient separation from a dilute solution of a compound capable of being separated through an affinity separation procedure, such as a protein from a dilute fermentation solution. The present invention provides a means for lessening the number of processing steps required to perform an affinity separation as compared to known affinity separation methods, thereby increasing the overall yield of the separation method. Indeed, the present inventive method can do away with the need for pretreatment of the fluid prior to contact with the affinity particles. Moreover, the present inventive method is able to be conducted in a relatively lesser amount of time as compared to known affinity separation processes. Further, since the present inventive method preferably utilizes nonporous affinity particles, the present invention avoids those problems attendant the use of porous affinity particles, e.g., affinity particle fouling, susceptibility to crushing, swelling, and low effective surface area. In addition, the present inventive method generally avoids problems of channeling, concentration wave phenomenon, and filtration medium fouling associated with conventional affinity separation methods.

The present inventive method comprises introducing the affinity particles and the fluid to be treated, i.e., a fluid containing a target compound to be isolated which is capable of adsorbing onto the affinity particles into a dynamic filtration apparatus. Such a dynamic filtration apparatus will desirably comprise motive means, a filtration medium having upstream and downstream sides, an inlet in fluid communication with the upstream side of the filtration medium, and a filtrate outlet in fluid communication with the downstream side of the filtration medium. The filtration medium has a pore rating which allows for the fluid being treated to entirely or substantially pass through the filtration medium without allowing the affinity particles to substantially pass through the filtration medium.

When the affinity particles and fluid to be treated are introduced into the dynamic filtration apparatus, the apparatus is configured so as to prevent any fluid from passing through the filtration medium, e.g., by use of appropriate valve means to close off the filtrate outlet. The motive means are then engaged (or may be engaged during the introduction of the affinity particles and fluid to be treated), so as to cause mixing of the target compound in the fluid being treated with the affinity particles to ensure their consistent interaction. This mixing process is continued for a satisfactory period of time, e.g., until the adsorption of the target compound onto the affinity particles has reached a maximum or equilibrium level. As a result of the consistent and reproducible interaction of the target compound and the affinity particles, the mixing process enables great precision in dealing with similar batches of fluid as to the quantity of affinity particles to be used in isolating the target compound and the time of interaction between the fluid containing the target compound and the affinity beads. Thus, the present inventive method provides for a rapid cycle process and the efficient and conserved use of affinity particles in permanent manufacturing processes wherein the similar fluids are being treated on a routine basis.

The affinity particles are then separated from the fluid by allowing the fluid to pass through the filtration medium. Such a separation may be accomplished by, for example, opening the filtrate outlet, while the motive means preferably continues to operate in the normal fashion. The affinity particles are then preferably washed with a suitable solution, e.g., washing buffer, so as to remove any residual fluid.

The target compound is recovered by eluting the compound from the affinity particles. Such elution may be carried out by any suitable technique, preferably by packing the affinity particles into a suitable receptacle, e.g., a column, and passing the eluent, e.g., desorbing agent, through the receptacle over the affinity particles to remove the target compound from the affinity particles. In order to minimize the amount of eluent and thereby increase the concentration of the recovered compound, the affinity particles are preferably packed as densely as possible into the elution receptacle. The target compound will typically be present in the eluent in a concentration at least about 10 times, preferably at least about 20 times, greater than the concentration of the target compound in the untreated fluid, i.e., the fluid prior to contact with the affinity particles. Most desirably, the quantity of eluent passed through the elution receptacle will be equivalent to about the free void volume, or at least no more than about two or three times the free void volume, of the elution receptacle, e.g., about one-half of the volume of a column densely packed with substantially monodisperse spherical affinity particles.

The relative sizes of the largest debris in the fluid to be treated, the pores of the filtration medium, and the diameter of the affinity beads are important in the practical utilization of the present inventive affinity separation method. Ideally, the filtration medium will allow all of the fluid (including the largest debris) to pass therethrough, while preventing any of the affinity particles from passing therethrough. The filtration medium, therefore, will preferably have a pore size at least a factor of two, and preferably a factor of five or ten, larger than the largest debris in the fluid to be treated, and the affinity particles will preferably be at least a factor of two, and preferably a factor of five or ten, larger than the pore size of the filtration medium. Thus, for example, if the largest debris in the fluid to be treated is on the order of about 0.1–0.2 micron, the pore size of the filtration medium will preferably be on the order of about 1–3 microns, while the affinity particles will preferably be on the order of about 10–20 microns.

In general, the smallest acceptable affinity particles, e.g., affinity particles of 60 microns diameter or less, particularly affinity particles of 20 microns diameter or less, are preferably used to improve the recovery of the target compound by increasing the available surface area per unit of weight of the affinity particles for interaction with the fluid being treating. Accordingly, while pretreatment of the fluid to be treated is generally undesirable in conjunction with the present inventive method inasmuch as it adversely impacts on the recovery of the target compound by introducing an additional processing step, there may be instances in which the recovery loss resulting from pretreatment, particularly prefiltering and/or homogenization, to reduce the size of the largest debris in the fluid will be more than offset by the resulting ability to use smaller affinity particles having a higher surface area per unit of weight of the affinity particles.

The present invention may be further understood with reference to the accompanying drawings. FIG. 1 schematically depicts the significant elements used in a preferred embodiment of the present invention. Upon commencement of the present inventive method, the fluid to be treated which contains the target compound to be separated from the remainder of the fluid resides in holding tank 1, while the affinity particles reside in holding tank 2. Both the fluid and the affinity particles are transferred to a buffer tank 3 where they are combined to form a mixture and preferably agitated, e.g., stirred. The mixture is then transferred to the dynamic filtration apparatus 4 via inlet 5, although the fluid and affinity particles could be directly transferred to the dynamic filtration apparatus 4 without passing through the buffer tank 3. The mixture is subjected to the mechanical agitation of the dynamic filtration apparatus 4 without any of the fluid passing through the filtration medium of the dynamic filtration apparatus 4, by, for example, the filtrate valve 7 being in the closed position.

After, or even during, suitable agitation, some or all of the mixture is transferred via concentrate valve 8 in a batch or continuous (in-line) process to a detection tank 9, wherein the concentration of the target compound in the fluid which remains unbound to the affinity particles is determined. Such detection, if desired, could also take place on a continuous or intermittent basis within the dynamic filtration apparatus 4. Furthermore, in a permanent manufacturing process wherein similar batches of fluid are being repeatably treated, there may be no need for any detection means after determining an appropriate quantity of fluid, affinity particles, and residence time in the dynamic filtration apparatus inasmuch as the present inventive method is quite consistent and reproducible as regards the recovery of the target compound. To the extent detection means are utilized, however, such detection means preferably control the opening and closing of filtrate valve 7, concentrate valve 8, and washing buffer valve 11, thereby controlling the flow direction of the mixture and the initiation and termination of the filtration process using the dynamic filtration apparatus 4.

If a separate detection tank 9 is utilized, and the concentration of unbound target compound in the fluid is greater than a preselected level, the mixture is transferred back to the dynamic filtration apparatus 4 via buffer tank 3 and the previously described methodology. This process is repeated until the concentration of unbound target compound in the fluid is below the preselected level, thereby indicating that a sufficient amount of the target compound has been adsorbed onto the affinity particles.

When it is determined, by whatever means, that a sufficient amount of target compound has been adsorbed onto the affinity particles, then the filtrate valve 7 is opened so that the fluid passes through the filtration medium of the dynamic filtration apparatus 4 into waste tank 6, thereby leaving the affinity beads in the dynamic filtration apparatus 4. The filtration valve 7 is then typically closed, although, alternatively, additional fluid can be passed into the dynamic filtration apparatus 4 for contacting with the affinity beads, particularly if the affinity beads are not saturated with the target compound. Such additional fluid can be passed into the dynamic filtration apparatus 4 in a continuous or semi-continuous manner while some of the fluid in the dynamic filtration apparatus 4 continues to pass through the filtration medium of the dynamic filtration apparatus 4.

After the addition of fluid into the dynamic filtration apparatus 4 is complete and the fluid within the dynamic filtration apparatus 4 has passed through the filtration medium of the dynamic filtration apparatus 4, the washing buffer valve 11 is opened to allow for washing buffer from washing buffer tank 10 to enter the dynamic filtration apparatus 4. The washing buffer is allowed to intermingle with the affinity particles for a suitable period of time, and then the filtrate valve 7 is again opened to allow for the washing buffer to pass to the waste tank 6. Typically, there will be several such wash cycles to ensure that the fluid being treated, except for the target compound bound to the affinity particles, has been removed from the dynamic filtration apparatus 4.

The affinity particles are then transferred to the elution receptacle 13 via the concentrate valve 8. Such a transfer may be accomplished by using washing buffer from the washing buffer tank 10 to transport the affinity particles to elution receptacle 13 into which they are preferably closely packed. Eluent valve 14 is then opened to allow for eluent from eluent tank 15 to pass through the elution receptacle 13 to remove the target compound from the affinity particles and pass the target compound through elution receptacle 13 for collection. As the effluent stream exits the elution receptacle 13, it preferably passes through an effluent detection means 16 which monitors the level of target compound in the effluent stream and closes the eluent valve 14 when the concentration of the target compound reaches a preselected level, e.g., about zero.

The affinity particles, which no longer have the target compound bound thereto, are then reused. Preferably, a suspension buffer is introduced into the elution receptacle 13 from a suspension buffer tank 12 so as to transfer the affinity particles from elution receptacle 13 to holding tank 2 for subsequent reuse.

By accurately timing the operations of the dynamic filtration apparatus 4 and the elution of compound in elution receptacle 13, the two devices can be simultaneously operated, thus converting batch processing into a semicontinuous process. FIG. 1, of course, is merely a schematic illustration of a preferred embodiment of the present invention, and the actual equipment and its placement may be varied considerably for other embodiments of the present invention. For example, the detection means 9 may be located separately from the dynamic filtration apparatus 4 or may be located in the dynamic filtration apparatus 4 so as to eliminate the need for transferring the mixture into and out of the dynamic filtration apparatus 4. Similarly, the detection means 16 may be located apart from or in elution receptacle 13, and the elution of the target compound from the affinity particles may take place in elution receptacle 13 or in any other suitable apparatus. Other variations will be apparent to those of ordinary skill in the art. Similarly, references to common components such as piping and pumping means have been omitted from FIG. 1, as well as from the above discussion, for purposes of clarity. The use of such components in the context of the present invention is well within the skill of those in the relevant art.

Affinity Particles

Any suitable affinity particles may be utilized in conjunction with the present invention. The affinity particles comprise a substrate and a ligand on the surface thereof which is capable of binding to the target compound in a fluid so as to enable the separation of that compound from the remainder of the fluid and then be capable of being removed from the affinity particles. Suitable affinity particles, including suitable substrates and ligands, are well known in the art. Many such affinity particles are used in the context of conventional affinity separation methods and would be equally or more usefully used in conjunction with the present inventive method. Of course, the affinity particles used to separate a particular compound from a particular fluid will vary, especially with respect to the ligand bound to the substrate surface of the affinity particle. The proper selection of the ligand will ensure that the target compound selectively and reversibly binds, e.g., complexes with or adsorbs onto, the affinity particle.

The affinity particles preferably have a surface which is smooth and nonporous (i.e., having pores of less than about 2000 angstroms in diameter or having no visible pores at 10,000 X magnification in a scanning electron micrograph), which is hydrophilic (i.e., having a critical wetting surface tension of at least about 72 dynes/cm), and which has a low susceptibility to nonspecific protein binding (i.e., binding only takes place through the attached ligands). The affinity particles are also preferably homogeneous between themselves, particularly as regards the quantity of ligand attached thereto, so as to provide consistent and predictable affinity separation results in the context of the present invention.

The affinity particles may be of any suitable shape but are preferably substantially spherical. Moreover, the affinity particles are preferably substantially monodisperse in diameter. Spherical affinity particles of similar size provide for the most efficient operation of the present inventive method, particularly with respect to the handling of the affinity particles. Such affinity particles generally will have the lowest probability of creating flow problems and will allow for the minimization of the size of the elution receptacle and quantity of eluent used to remove the target compound from the affinity particles as a result the more uniform and dense packing which can be achieved with such affinity particles.

The affinity particles may be of any suitable size. The average diameter of the affinity particles will typically be less than about 100 microns, and more usually less than about 60 microns. Preferably, the affinity particles will have an average diameter of less than about 20 microns, and more preferably less than about 10 microns. For many uses, the affinity particles will advantageously have a diameter of about 1 to about 5 microns. As previously described, the affinity particles preferably are substantially monodisperse in diameter, such that the range of diameters preferably does not differ by more than about 50%, more preferably about 25%, and most preferably about 10%, as determined by dividing the diameter of the smallest particle by the diameter of the largest particle. The diameters of the affinity particles can be determined by known means, such as through use of scanning electron micrographs.

In any event, it is desirable that substantially all of the affinity particles not pass through the filtration medium, since the affinity particles which do so represent a loss in affinity particles as well as a decrease in the recovery of the target compound given that such a pass-through would take place after the target compound had bound to the affinity particles. In order to avoid such a loss in affinity particles, the substrate particles are preferably subjected to the filtration medium to be used in the dynamic filtration apparatus prior to further processing. In this manner, substrate particles which would pass through the filtration medium are removed prior to the attachment of the ligand which will bind the target compound. The efficiency of the overall affinity separation method is thereby improved by ensuring the near absolute recovery of the affinity particles with the bound target compound and narrowing the size distribution of the affinity particles for improved handling. The size distribution of the thus obtained affinity particles can be further improved by changing the filtration medium to one having a larger pore size and subjecting the substrate particles to the dynamic filtration process yet again. The recovered substrate particles which passed through the filtration medium in this second pass would have an even narrower size distribution (substantially limited at the low end by the pore size of the first filtration medium and substantially limited at the high end by the pore size of the second filtration medium). While such sizing control methods are preferably carried out on the substrate particles prior to attachment of the ligand thereto, the techniques, of course, can also be used to size the affinity particles (i.e., after attachment of the ligand to the substrate particles).

The affinity particles may have any suitable density. The affinity particles advantageously have an average density ranging from about 0.5 g/cm$^3$ to about 3.0 g/cm$^3$, preferably about 1 g/cm$^3$ to about 2 g/cm$^3$, and most preferably about 1 g/cm$^3$, to ensure adequate buoyancy of the media during processing.

Substrate Particles

Any suitable substrate may be used to prepare the affinity particles. As discussed above, the surface of the affinity particles is preferably smooth, nonporous, and hydrophilic, and has a low susceptibility to the adsorption of compounds, particularly proteins. The substrate can be a homogeneous material, which preferably satisfies the aforesaid preferred characteristics, or may comprise more than one material (e.g., a core material coated with another material), the surface layer of which preferably satisfies the aforesaid preferred characteristics. Thus, for example, the substrate particles may comprise a homogeneous nonporous material, a porous core material coated with a nonporous polymeric material, or even a nonporous core material coated with a nonporous polymeric material. While the substrate particles may comprise, for example, a homogeneous porous material or even a core material coated with a porous material, such substrate particles are not preferred for use in the present inventive method.

The substrate particles are preferably prepared from glass, alumina, steel (particularly stainless steel), silica, SiAl, diatomaceous earth, or, preferably, a polymeric material, such as, for example, polystyrene, polyethylene, polytetrafluoroethylene, cellulose, cellulose esters, polycarbonate, polystyrene, acrylonitrile-butadiene-styrene copolymer, polyphenylene oxide polymer, polysiloxane, and latex. The exposed surface of the substrate must allow for the binding of a suitable ligand, which will not become unbound during further processing. The substrate should be mechanically stable, nonswelling, and nonreactive when exposed to the fluid to be treated. Other characteristics of the substrate will vary with the particular fluid to be treated and target compound to be separated therefrom. For example, the substrate can be selected such that the affinity particles possess a desired degree of buoyancy. Particularly useful substrates for the affinity separation of proteins include high and low density polyethylenes in the Microthene Series available from Quantum Chemical (specific gravity: 0.92–0.96; surface area: <1 m$^2$/g; average size: about 20 microns, with about 10% of the particles being over about 50 microns which can be separated out) and PTFE-30 available from DuPont (average size: about 0.1 to 0.5 microns).

To the extent the substrate is coated to render the substrate smooth, nonporous, hydrophilic, and/or less susceptible to protein binding, any polymer can be utilized as the coating material so long as a suitable ligand can be attached thereto for use in isolating the target compound. Any suitable method of attaching a polymeric coating to a core material may be utilized. Thus, for example, methods such as monomer radiation grafting (particularly electron beam grafting) and polymeric solution coating may be satisfactorily used.

Modified cellulose and cellulosic derivatives, such as cellulose acetate, are biocompatible polymers which are generally quite useful in the context of the present invention. Such modified cellulosic derivatives include cellulosic polymers surface modified by covalently linking pendant biocompatible surface groups to the cellulosic substrate polymer rendering it more biocompatible. While many suitable surface groups are well-known in the art, albumin has shown particular utility as such a modifying group. Suitable polymers for surface coating core materials include homopolymers and copolymers which can be prepared from a wide variety of monomers. For example, monomers particularly suitable for radiation grafting include acrylic and methacrylic acids (particularly, hydroxyalkyl acrylates and hydroxyalkyl methacrylates, e.g., hydroxyethyl acrylate, hydroxypropyl acrylate, and hydroxybutyl methacrylate) and allyl alcohols. Polymers particularly suitable for solution coating include hydroxy functional polymers such as allyl alcohols, polyvinyl alcohols, polyacrylamides, vinyl glycidyl ethers, and allyl glycidyl ethers. Many other monomers and polymers can, of course, be used in preparing affinity particles for use in the context of the present invention.

The surface of the substrate, whether a homogeneous or a coated-core type substrate, is preferably such that it possesses a low or no affinity for the target compound in the fluid being treated. Such a surface ensures that the target compound will reversibly complex or otherwise attach to the ligand on the surface of the substrate particles rather than the surface of the substrate particles per se where the target compound may be too weakly or too strongly attached so as to be lost or unrecoverable in further processing. The substrate surface is also preferably spontaneously wettable by the fluid being treated, e.g., hydrophilic, to ensure good contact between the affinity particles and the fluid being treated and, thereby, good recovery of the target compound from the fluid being treated. Moreover, the surface of the substrate is preferably smooth to minimize adherence of material other than the target compound to the attached ligand on the surface of the affinity particles and to provide for easy cleaning of the affinity particles. The substrate is preferably capable of being reused many times and should be chemically stable such that it does not decompose or otherwise pose contamination problems.

Ligand

The ligand can be any chemical functionality that can be attached to substrate particles without being removed during subsequent processing and will selectively bind with the target compound, such as antibodies, antigens, proteins, nucleic acids, complement components, hormones, vitamins, and the like. The ligand will typically be provided by reacting a particular compound having the desired functionality with the substrate particles, but may also be an integral part of the substrate particle, e.g., of the polymeric coating on a core material.

Methods for attaching the ligand to the substrate particles are well-known to those in the art. Suitable attachment methods include spontaneous covalent attachment, chemical activation of terminal functional groups, and coupling reagent attachment.

Spontaneous covalent attachment of certain ligands to polymer support surfaces proceeds via chemically reactive groups extending from the polymer support. Thus, for example, reactive groups such as aldehyde and epoxy extending from the polymer support readily couple ligands containing available hydroxyl, amino, or thiol groups. Also, for example, free aldehyde groups on the polymer support coupled via acetal linkages with hydroxyl-containing compounds and via imide linkages with amino-containing compounds. Additionally, for example, free oxime groups couple via alkylamine, ether, and thioether linkages with compounds containing amine, hydroxyl, and thio groups respectively. More extensive discussions of these reactions may be found, for example, in Chen et al., "Chemical Procedures for Enzyme Immobilization of Porous Cellulose Beads," *Biotechnology and Bioengineering*, XIX, 1463–1473 (1977), and in "Epoxy Activated Sepharose," *Pharmacia Fine Chemicals* (Affinity Chromatography), 6B, 27–32 32 (1979).

Chemical activation of terminal functional groups may be accomplished by activating polymer surface functional groups by chemical modification of their terminal components. This method can be exemplified by the oxidation of terminal epoxy functions with periodic acid to form active aldehyde groups. This method is further exemplified, for example, in Svec et al., "Immobilization of Amyloglucosidose on Poly [(Glycidyl Methacrylate) Co (Ethylene Dimethacrylate)] Carrier and Its Derivatives," *Biotechnology and Bioengineering*, XX, 1319–1328 (1978). The immobilization of the ligand such as a ligand can proceed as described above. Condensation reactions may be accomplished between free carboxyl and amine groups via carbodiimide activation of the carboxy groups as is described, for example, in Hoffman et al., "New Approaches to Non-Thrombogenic Materials," *Coagulation-Current Research and. Clinical Applications*, (Academic Press, New York 1973). The immobilization of the ligands is effected by carbodiimide activation by either the polymer or ligand carboxyl groups and condensation with a free amine to form a stable peptide bond. The final orientation of the ligand is generally a factor as to whether an amine or a carboxyl containing polymer is utilized.

Coupling reagent attachment can be accomplished using a variety of coupling agents to form covalent bridges between polymers and ligands. Free hydroxyl and/or amine containing polymers and ligands can be covalently coupled by reagents such as, for example, cyanogen bromide, diisocyanates, dialdehydes, and trichloro-s-triazine. A more exhaustive discussion of this technique may be found, for example, in the Chen et al. reference cited hereinabove.

The preferred method of immobilizing a ligand onto a polymer substrate in a given case is generally dictated by the molecular locations of the reactive binding moiety of the ligand and the particular functional groups of the ligand and polymer substrate which can be covalently combined. For example, it is presently preferred in the case of polymer substrates containing terminal hydroxy functions to activate by treatment with an alkaline solution of cyanogen bromide (e.g., 10–20% w/v). Typically the reaction mixture is maintained at room temperature (e.g., 20°–25 °C.) for about 30 minutes. The pH of the solution is maintained in a range of about 10 to 12 by the addition of alkaline material, e.g., KOH or NaOH. The polymer is then extensively washed with physiological saline (0.9 gm %) and incubated with solutions of a purified ligand dissolved in a slightly alkaline buffer solution for 12–16 hours at 2°–8° C. The polymer is extensively rinsed with physiological saline to remove unbound or nonspecifically bound ligands.

Similarly, ligands are preferably immobilized on glycidyl containing polymers via ether, thioether, or alkylamine bonds. Epoxy-activated polymer substrates are rinsed and swollen with aqueous neutral buffer solutions at room temperature. Purified ligands, dissolved borate, carbonate or phosphate buffer solutions are incubated with glycidyl polymer substrate for 12–20 hours at 4°–30° C. Excess and nonspecifically bound ligands are removed by rinsing the polymer with saline, acetic acid (0.2–1.0M), and phosphate-buffered (pH=7.2±0.2) saline solutions. Activation of amine and carboxyl containing polymer matrices is effected by treatment with purified ligands dissolved in slightly acidic (pH=4.5–6.5) buffer solutions of a water-soluble carbodiimide. The ligands are covalently coupled to a polymer substrate by incubation of the polymer substrate, ligand, and carbodiimide reactants for 12–16 hours at 2°–8° C. The polymer-ligand conjugates are washed alternately in acid and then alkaline rinses until the rinse solutions are clear of ligand and carbodiimide reactants.

By way of further example, a method of binding ligands to the surface of substrate particles is described in U.S. Pat. No. 5,077,210. A silane is bound to the substrate and couples to a heterobifunctional crosslinker at one functional group of the ligand, thereby leaving a different functional group which is free to bind the target compound, such as a protein. Preferably, the silane has a functional group which reacts with the hydroxyl group of the substrate and a thiol terminal group which reacts with a functional group of a heterobifunctional crosslinking agent which contains a succinimide group for subsequent reaction with an amino group of a target compound, such as a protein.

A method of binding antibodies to the surface of substrate particles is described by U.S. Pat. No. 4,357,311. This method involves covalently bonding an antibody through trichloro-triazine to yield the affinity particles. Further, numerous methods for immobilizing enzymes on the surface of substrate particles are disclosed in "Enzyme Technology" (Noyes Data Corporation 1983), particularly at pages 38 to 59 thereof.

Spacers may also be utilized in preparing affinity particles for use in the present inventive affinity separation method. A spacer is generally a molecule which has at least two reactive functional groups, which may be the same or different, situated at opposing ends of the molecule and is used to link the substrate particles and the ligand. Spacers can be used to facilitate the attachment of a ligand to substrate particles and to insure that the ligand is held sufficiently away from the substrate particles so as to more efficiently contact the fluid being treated and, more particularly, the target compound. Suitable spacers in which the reactive functional groups are the same include, for example, 6-diaminohexane, divinyl sulfone, glutaraldehyde, 1,4-cyclohexanedicarboxylic acid, ethylenediamine tetraacetic acid, triethylene glycol, 1,4-butanediol diglycidyl ether, methylene-p-phenyl diisocyanate and succinic anhydride. Suitable spacers in which the reactive functional groups are not the same include, for example, 6-aminocaproic acid, p-nitrobenzoyl chloride, 1,2-epoxy-3-(p-nitrophenoxy) propane, aminopropyltriethoxy-silane, and homocysteine thiolactone. Polypeptides, and more specifically proteins, may also be used as spacers. Albumin, a low affinity protein, for example, has been successfully employed as a spacer, and albumin and other natural proteins also serve to render the substrate particles more biocompatible.

Dynamic Filtration Apparatus

The dynamic filtration apparatus may be any suitable dynamic filtration apparatus. The operating principle of a dynamic filtration apparatus is to maintain a filtration medium free from plugging or fouling by repelling particulate matter from the filtration medium and by disrupting the formation of cake layers adjacent to the filtration medium. These results are accomplished by moving the fluid stream fast enough relative to the filtration medium to produce high shear rates as well as high lift forces on the particulates, preferably by use of rotating means operating within the dynamic filtration apparatus which act upon the fluid being treated, although other means, such as oscillating and reciprocating means, can be similarly used to achieve a similar effect. The shear at the fluid-filtration medium interface in a dynamic filtration process is nearly independent of any cross-flow fluid velocity, unlike tangential or cross-flow filtration techniques (which suffer from other problems such as premature filter plugging due to compound adsorption and large and nonuniform pressure drops associated with high tangential velocities along the filter length, potentially causing backflow through the filtration medium and reducing filtration).

Dynamic filtration offers a number of performance advantages in the context of the present invention. The very high shear rates produced in the dynamic filtration assembly provide an excellent means for ensuring that the affinity particles are thoroughly contacted by the fluid being treated so as to ensure a high rate of recovery of the target compound. Moreover, since increases in permeate flux rate have been observed to be approximately linear with increased shear rate in some systems, the filtration area required to efficiently remove the fluid being treated from the affinity particles can be dramatically reduced over other filtration means.

A typical dynamic filtration apparatus comprises an outer impermeable housing and an inner element which contains the filtration medium that moves relative to the fluid. A variety of suitable motive means can be utilized to carry out such relative motion, such as, for example, rotational, oscillation, or reciprocating means. Suitable cylindrical dynamic filtration systems are disclosed in U.S. Pat. Nos. 3,797,662, 4,066,554, 4,093,552, 4,427,552, 4,900,440, and 4,956,102. Suitable rotating disc dynamic filtration systems are disclosed in U.S. Pat. Nos. 3,997,447, 4,956,102, and 5,037,562, as well as in U.S. patent application Ser. No. 07/812,123, filed on Dec. 24, 1991. Other suitable dynamic filtration systems are disclosed in U.S. Pat. Nos. 4,952,317. Suitable commercially available dynamic filtration assemblies include ASEA Brown Bovery rotary CROT, New Logic V-SEP, and the filtration devices discussed in Murkes, "Fundamentals of Crossflow Filtration," *Separation and Purification Methods*, 19(1), 1–29 (1990). Other suitable configurations for the dynamic filtration apparatus can also be used in the context of the present invention. Within the context of the present invention, the dynamic filtration apparatus preferably produces shear rates of at least about 5,000 sec$^{-1}$, and more preferably at least about 10,000 sec$^{-1}$.

The filtration medium used in conjunction with the dynamic filtration apparatus can be any suitable filtration medium and will typically be a porous membrane, preferably a microporous polymeric membrane. While the filtration medium may have any suitable pore rating, e.g., about 20 microns or less, about 10 microns or less, about 5 microns or less, or even about 1 micron or less, the filtration medium will preferably allow for all, or at least substantially all, of the fluid being treated to pass through the filtration medium while retaining all, or at least substantially all, of the affinity particles. Thus, the pore rating of the filtration medium is largely dependent on the size of the affinity particles and the size of the largest debris (i.e., nontarget compound) in the fluid being treated.

Figure 2:
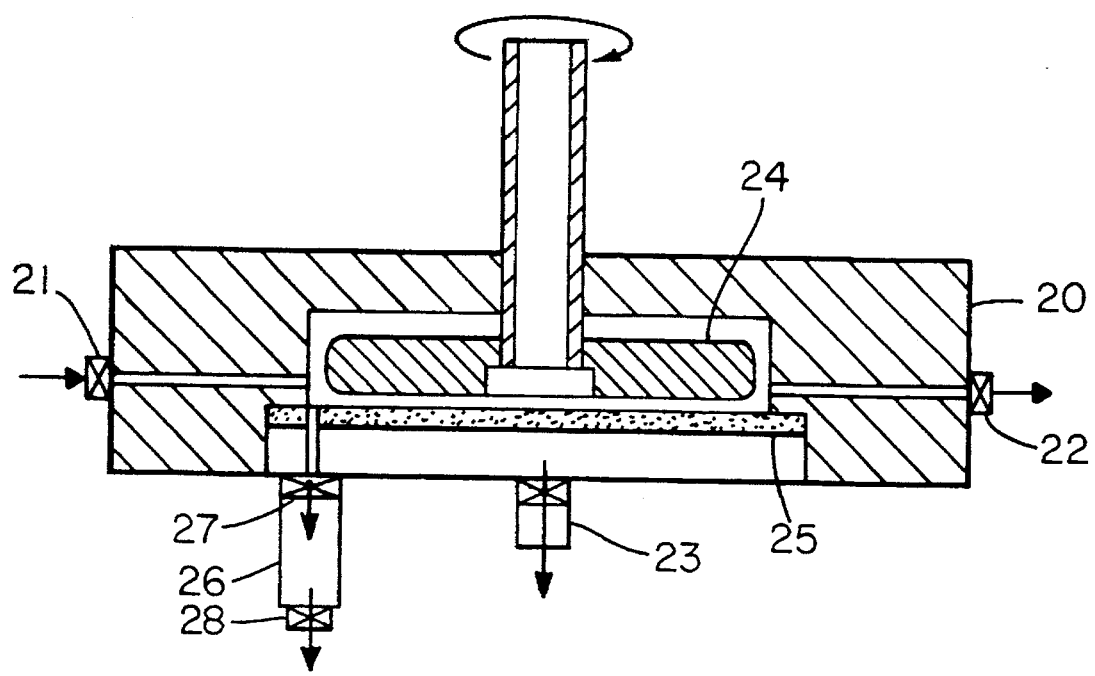
FIG. 2 is a schematic depiction of a preferred dynamic filtration apparatus for use with the present inventive affinity separation method.

FIG. 2 schematically depicts a preferred dynamic filtration apparatus for use with the present inventive affinity separation method. The dynamic filtration apparatus comprises a housing 20 having a feed port 21, a concentrate port 22, and a filtrate port 23. A rotating means 24 is disposed within the housing 20 along with a filtration medium 25. The feed port 21 and concentrate port 22 are in fluid communication with the upstream side of the filtration medium 25, while the filtrate port 23 is in fluid communication with the downstream side of the filtration medium 25. Fluid is capable of passing through the filtration medium 25, while affinity particles are substantially incapable of passing through the filtration medium 25. An elution receptacle 26 is in fluid communication with the upstream side of the filtration medium 25 and is connected to the housing 20 by means of an elution receptacle inlet valve 27 which can control the flow of the affinity particles and fluids into the top of the elution receptacle 26. The elution receptacle 26 also has an elution receptacle outlet valve 28 at the bottom of the elution receptacle 26 which can control the inflow and outflow of fluids into the elution receptacle 26.

In use, a mixture of the fluid containing the target compound and the affinity particles are fed into the housing 20 of the dynamic filtration apparatus via feed port 21. The rotating means 24 are activated for a sufficient period of time to effect binding of the target compound with the affinity particles within the dynamic filtration apparatus, with the concentrate port 22 and filtrate port 23 being closed so that none of the mixture may pass through the filtration medium 25.

The mixture is then filtered through filtration medium 25 by opening filtrate port 23 to allow the fluid to be removed from within the dynamic filtration apparatus. Washing buffer may be introduced into the dynamic filtration apparatus via feed port 21 to remove any unbound material from within the dynamic filtration apparatus, and the washing buffer may then be allowed to pass through the filtrate port 23. Multiple washing steps, if desirable, can of course be carried out in the same manner. The affinity particles are then transferred to the elution receptacle 26 via elution receptacle inlet valve 27, preferably by the introduction of a small quantity of washing buffer into the dynamic filtration apparatus. In order to ensure that the entire dead volume of the dynamic filtration apparatus is efficiently and completely drained into the elution receptacle 26, the dynamic filtration apparatus is preferably displaced somewhat, e.g., 5°–10°, from horizontal with the elution receptacle located at the low point of the dynamic filtration apparatus.

Eluent is then introduced into the elution receptacle 26, e.g., via feed port 21 and elution receptacle inlet valve 27, to remove the target compound from the affinity particles, which can be drawn off the elution receptacle 26 via elution receptacle outlet valve 28. After the target compound has been removed from the affinity particles and recovered, the affinity particles can then be reused by, for example, introducing a suspension buffer into the elution receptacle 26 via elution receptacle outlet valve 28 to transfer the affinity particles back into the dynamic filtration apparatus via elution receptacle inlet valve 27. The suspension buffer may then be removed, if desired, by way of filtrate port 23, and the process repeated with additional fluid containing the target compound.

FIG. 2, of course, is merely a schematic illustration of a preferred embodiment of apparatus useful in the carrying out the present inventive method, and particular aspects of an actual apparatus for use with the present invention may be varied considerably. For example, detection means may be located within the dynamic filtration apparatus to determine the quantity of unbound target compound. Similarly, a detection means may be located apart from or in the elution receptacle to determine the quantity of target compound eluted from the affinity particles. Other variations will be apparent to those of ordinary skill in the art. Similarly, references to common components such as piping and pumping means have been omitted from FIG. 2, as well as from the above discussion, for purposes of clarity. The use of such components in the context of the present invention is well within the skill of those in the relevant art.

Illustrative Uses

The present inventive method may be used to separate or isolate any compound from any fluid so long as the compound and fluid are suitable for affinity separation. For example, the present inventive method can be used to isolate proteins and antibodies from fluids such as fermentation products, milk, and whole blood or serum. The present inventive method can also be used to isolate a particular stereoisomer from a racemic mixture.

The present inventive method is particularly well-suited for the isolation or separation of a protein from a dilute protein-laden fermentation broth inasmuch as the present inventive method does not require that the broth be pretreated to remove unwanted contaminants, e.g., cell debris, pyrogens, pathogens, or toxins.

Various other combinations of ligands and target compounds are set forth below:

| Ligand | Target Compound |
|---|---|
| inhibitor; cofactor; prosthetic group; polymeric substrate | enzymes; apoenzymes |
| enzyme | polymeric inhibitors |
| nucleic acid (single strand) | nucleic acid (complementary strand) |
| hapten; antigen | antibody |
| antibody | proteins; polysaccharides |
| monosaccharide; polysaccharide | lectins; receptors |
| lectin | glycoproteins; receptors |
| small target compound | binding proteins |
| binding protein | small target compounds |

Further such ligand-target compound relationships are known to those of ordinary skill in the art and can be used in the context of the present inventive affinity separation method.

All of the references cited herein, including publications, patents, and patent applications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of affinity separation for isolating a target compound from a fluid comprising:
   (a) introducing
     (1) a fluid containing a target compound to be isolated, and
     (2) affinity particles capable of adsorbing the target compound
   into a dynamic filtration apparatus comprising
   motive means, a porous filtration medium having an upstream side and a downstream side, an inlet in fluid communication with the upstream side of said filtration medium, and a filtrate outlet in fluid communication with the downstream side of said filtration medium, wherein said fluid is capable of passing through said filtration medium and said affinity particles are incapable of passing through said filtration medium,
   (b) closing said filtrate outlet of said dynamic filtration apparatus and preventing the passage of said fluid through said filtration medium,
   (c) mixing said affinity particles and said fluid in said dynamic filtration apparatus by operating said motive means of said dynamic filtration apparatus and adsorbing said target compound onto said affinity particles, wherein operating said motive means moves said fluid relative to said filtration medium and creates a shear at the fluid-filtration medium interface which is nearly independent of any cross-flow fluid velocity,
   (d) opening said filtrate outlet of said dynamic filtration apparatus and passing said fluid through said filtration medium of said dynamic filtration apparatus,
   (e) washing said affinity particles, and
   (f) eluting said target compound from said affinity particles.

2. The method of claim 1, wherein said affinity particles are nonporous.

3. The method of claim 2, wherein said affinity particles are spherical.

4. The method of claim 3, wherein said affinity particles are monodisperse in diameter.

5. The method of claim 4, wherein said affinity particles have a diameter at least about two-fold larger than the pore size of said filtration medium.

6. The method of claim 5, wherein said fluid contains particulates and said filtration medium has a pore size at least about two-fold larger than the size of the largest particulate in said fluid.

7. The method of claim 4, wherein said affinity particles have a diameter at least about five-fold larger than the pore size of said filtration medium.

8. The method of claim 7, wherein said fluid contains particulates and said filtration medium has a pore size at least about five-fold larger than the size of the largest particulate in said fluid.

9. The method of claim 3, wherein the range of diameters of said affinity particles does not differ by more than about 10% as determined by dividing the diameter of the smallest particle by the diameter of the largest particle.

10. The method of claim 1, wherein the concentration of said target compound in said fluid is monitored.

11. The method of claim 1, wherein said separation step (c) is carried out when the concentration of said target compound in said fluid reaches a preselected level.

12. The method of claim 1, wherein said target compound is eluted from said affinity particles by transferring said affinity particles having said target compound bound thereto from said dynamic filtration apparatus into an elution receptacle, passing an eluent through said elution receptacle to remove said target compound from said affinity particles, thereby providing eluted affinity particles from which said target compound has been removed, and collecting the resulting eluent containing said target compound.

13. The method of claim 12, wherein said target compound is present in said resulting eluent in a concentration at least about 10 times greater than the concentration of said target compound in said fluid containing a target compound to be isolated prior to contact with said affinity particles.

14. The method of claim 12, wherein the volume of eluent passed through said elution receptacle is equal to about the free void volume of said elution receptacle.

15. The method of claim 12, wherein said eluted affinity particles are then transferred back to said dynamic filtration apparatus and the method repeated.

16. The method of claim 15, wherein said elution receptacle has an inlet and an outlet and the inlet of said elution receptacle is in fluid communication with the upstream side of said filtration medium of said dynamic filtration apparatus.

17. The method of claim 1, wherein said dynamic filtration apparatus is operated to achieve a shear rate of at least about 5,000 $sec^{-1}$.

18. The method of claim 17, wherein said dynamic filtration apparatus is operated to achieve a shear rate of at least about 10,000 $sec^{-1}$.

19. The method of claim 1, wherein said target compound is a protein.

20. The method of claim 19, wherein said fluid containing a target compound to be isolated is a fermentation broth.

21. The method of claim 19, wherein said fluid containing a target compound to be isolated is milk.

22. The method of claim 1, wherein said target compound is an antibody.

23. The method of claim 22, wherein said fluid containing the antibody is whole blood or serum.

24. The method of claim 1, wherein said fluid containing a target compound to be isolated is a racemic mixture of stereoisomers and said target compound is on of said stereoisomers.

25. The method of claim 1, wherein said target compound is biologically active.

26. The method of claim 1, wherein said affinity particles have an average diameter of about 60 μ or less.

27. The method of claim 26, wherein said affinity particles have an average diameter of about 20 μ or less.

28. The method of claim 27, wherein said filtration medium has a pore rating of less than about 5 μ.

29. The method of claim 1, wherein said affinity particles have an average diameter of at least about 1 μ.

30. The method of claim 29, wherein said filtration medium is a microporous membrane having a pore rating of less than about 1 μ.

31. A method according to claim 1, wherein said affinity particles comprises a core material and a polymer coating thereon which is nonporous and hydrophilic.

32. The method of claim 31, wherein said polymer coating has been formed by radiation grafting monomers onto said core material.

33. The method of claim 32, wherein said monomers are selected from the group consisting of acrylic and methacrylic acids.

34. The method of claim 31, wherein said core material is porous.

* * * * *